United States Patent [19]

Baldwin et al.

[11] Patent Number: 5,091,409
[45] Date of Patent: Feb. 25, 1992

[54] 4-ALKYLAMINO-6-(C$_{3-5}$-HYDROCARBYL)-THIENO[2,3-B]THIOPYRAN-2-SULFONAMIDE-7,7-DIOXIDES

[75] Inventors: John J. Baldwin, Gwynedd Valley; Gerald S. Ponticello, Lansdale; Kenneth L. Shepard, North Wales; Theresa M. Williams, Harleysville, all of Pa.

[73] Assignee: Merck & Co., Inc., Rahway, N.J.

[21] Appl. No.: 524,523

[22] Filed: May 17, 1990

[51] Int. Cl.$^5$ ............... A61K 31/38; C07D 335/04
[52] U.S. Cl. .................... 514/434; 549/23; 514/432
[58] Field of Search ............. 549/23; 514/432, 434

[56] References Cited

U.S. PATENT DOCUMENTS

| | | |
|---|---|---|
| 4,386,098 | 5/1983 | Woltersdorf, Jr. ............ 424/270 |
| 4,416,890 | 11/1983 | Woltersdorf, Jr. ............ 424/270 |
| 4,426,388 | 1/1984 | Woltersdorf, Jr. ............ 424/270 |
| 4,503,066 | 3/1985 | Brittain ........................ 549/23 |
| 4,668,697 | 5/1987 | Shepard et al. ............... 514/443 |
| 4,863,922 | 9/1989 | Baldwin ..................... 514/232.5 |

OTHER PUBLICATIONS

Ponticello, "Thienothiopyran-2-sulfonamides...", J. Med. Chem., 1987, 30, 591–597.

Primary Examiner—Alan L. Rotman
Assistant Examiner—Catherine Scalzo
Attorney, Agent, or Firm—Donald J. Perrella; Joseph F. DiPrima

[57] ABSTRACT

4-Alkylamino-6-(C$_{3-5}$-hydrocarbyl)thieno[2,3-b]thiopyran-2-sulfonamide-7,7-dioxides wherein the 4-alkylamino group is an ethylamino or propylamino are powerful carbonic anhydrase inhibitors useful in the treatment of ocular hypertension and glaucoma associated therewith.

10 Claims, No Drawings

4-ALKYLAMINO-6-(C$_{3-5}$-HYDROCARBYL)-THIENO[2,3-B]THIOPYRAN-2-SULFONAMIDE-7,7-DIOXIDES

SUMMARY OF THE INVENTION

This invention is concerned with a compound of structural formula:

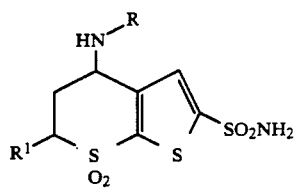

or an ophthalmologically acceptable salt thereof wherein R is ethyl or propyl and R$^1$ is a C$_{3-5}$ hydrocarboyl group which is useful in the treatment of ocular hypertension and glaucoma associated therewith.

This invention also relates to pharmaceutical compostions and the use thereof for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing introcular pressure, they also have other characteristics, e.g. membrane stabilizing activity, that are not acceptable for chronic ocular use. (S)-1-tert-Butylamino[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g., to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. U.S. Pat. No. 4,668,697 discloses substituted benzo[b]thiophene-2-sulfonamides as carbonic anhydrase inhibitors useful in the treatment of ocular hypertension.

Also, U.S. Pat. Nos. 4,797,413 and 4,677,115, disclose that certain thieno[2,3-b]thiopyran-2-sulfonamides have the utility of interest. In particular U.S. Pat. No. 4,797,413, the disclosure of which is incorporated herein by reference, generically discloses and claims some of the novel compounds of the present invention.

DETAILED DESCRIPTION OF THE INVENTION

The novel compound of this invention has structural formula I:

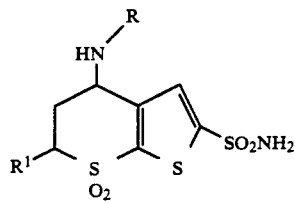

or an ophthalmologically acceptable salt thereof wherein
R is ethyl, n-propyl or iso-propyl; and
R$^1$ is
a) C$_{3-5}$ alkyl, either straight or branched chain, especially n-propyl or isobutyl;
b) C$_{3-5}$ alkenyl, especially allyl; or
c) C$_{3-5}$ alkynyl, especially propargyl.

Also included within the scope of this invention are the individual diastereomers, the individual enantiomers and mixtures thereof.

The ophthalmologically acceptable salts include such as hydrochloride, hydrobromide, maleate, isethionate, fumarate, citrate or the like.

The most preferred species of the compound of formula I is 4-ethylamino-6-n-propylthieno[2,3-b]-thiophene-2-sulfonamide-7,7-dioxide and the 6-allyl analog and especially the trans (−) (S,S)- and cis (+), (S,R)-isomers thereof.

The especially preferred compounds of this invention, the (S,R)- and (S,S)- enantiomers of 5,6-dihydro-4-ethylamino-6-(n-propyl)-4H-thieno[2,3-b]thiopyran-2-sulfonamide-7,7-dioxide and the 6-allyl analog have unexpected advantageous properties relative to their nearest structural relatives disclosed in U.S. Pat. No. 4,863,922. These properties are the intrinsic carbonic anhydrase inhibition activity (I$_{50}$) and Ki determined by the methods described by Ponticello et al., *J. Med. Chem.*, 30, 591 (1987) as shown in the following Table:

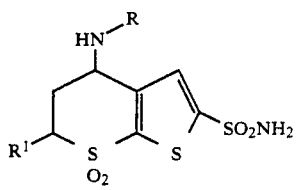

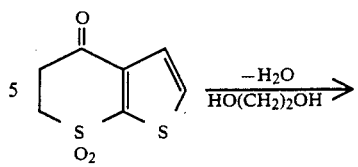

| Compound | R$^1$ | R | Isomer | I$_{50}$ (nM) | K$_i$ (nM) |
| --- | --- | --- | --- | --- | --- |
| 1 | n-C$_3$H$_7$— | C$_2$H$_5$— | trans (−) | 0.26 | 0.14 |
| 2 | n-C$_3$H$_7$— | C$_2$H$_5$— | cis (+) | 0.19 | 0.17 |
| 3 | n-C$_3$H$_7$— | C$_3$H$_7$— | trans (−) | 0.15 | 0.23 |
| 4 | C$_2$H$_5$— | CH$_3$— | trans (+) |  | 3.6 (1.8 hi)* |
| 5 | C$_2$H$_5$— | CH$_3$— | cis (+) |  | 7.1 (2.6 hi) |
| 6 | C$_3$H$_7$— | CH$_3$— | trans (+) |  | 2.1 (0.85 hi) |
| 7 | C$_3$H$_7$ | CH$_3$— | cis (+) |  | 2.8 (0.64 hi) |
| 8 | CH$_3$— | C$_2$H$_5$— | trans (−) | 0.24 | 0.28 |
| 9 | CH$_3$— | C$_2$H$_5$— | cis (+) | 1.1 | 2 |
| 10 | C$_2$H$_5$— | C$_2$H$_5$— | trans (−) | 0.5 | 0.3 |
| 11 | C$_2$H$_5$— | C$_2$H$_5$— | cis (+) | 0.8 | 1 |
| 12 | CH$_2$=CHCH$_2$— | C$_2$H$_5$— | trans (−) | 0.23 |  |
| 13 | CH$_2$=CHCH$_2$— | C$_2$H$_5$— | cis (+) | 0.21 | 0.4 |
| 14 | (CH$_3$)$_2$CHCH$_2$— | C$_2$H$_5$— | cis (+) | — | 2.6 (0.13 hi) |

*hi = more active component of racemic mixture

Compounds 1 and 13 of the foregoing table are also unexpectedly active relative to the corresponding prior art 6-methyl analog, Compound 8, in the ocular hypertensive monkey (Lee et al., Curr. Eye Res., 4,775–781 (1985)). At 16 hours after treatment, Compounds 1 and 13 produced drops in IOP of 11.3 and 9.8 mmHg respectively, whereas compound 8, produced a drop in IOP of only 5.6 mm Hg.

The novel compounds of this invention can be prepared by reduction of the appropriate 4-N-acyl analogs in an ethereal solvent such as THF, diethyl ether, or 1,2-dimethoxyethane at about 55°–75° C. by dropwise addition of the borane-dimethylsulfide complex followed by isolation of the product about 1–2 hours after the addition is complete.

Alkylamino groups are also available from the corresponding 4-hydroxy compounds by treatment of the 4-hydroxy with toluenesulfonyl chloride in pyridine at about −20° C. to 5° C. for about 3 to 10 hours followed by the addition of an alkylamine at a temperature below about 15° C. followed by warming to about 30°–60° C. for about 5 to 16 hours.

4-Alkylamines are also prepared from the 4-oxo compounds by treatment with titanium tetrachloride and the appropriate amine followed by reduction with a complex metal hydride. In this process a solution of the keto compound in a solvent such as diethylether, THF, 1,2-dimethoxy-ethane, benzene, toluene or mixtures thereof at about −20° C. to 0° C. is treated quickly with about a one molar excess of an amine of formula RNH$_2$ followed by titanium tetrachloride dropwise. After about 1 to 5 hours the mixture is filtered and evaporated. The residue is treated with a complex metal hydride, such as sodium borohydride, in excess in a C$_{1-3}$alkanol, preferably methanol, at about room temperature for up to 24 hours. Excess hydride is destroyed with aqueous acid and the product is isolated by standard techniques.

An alternate process for introduction of the 6-substituent in the synthesis of the novel compounds of this invention is depicted as follows:

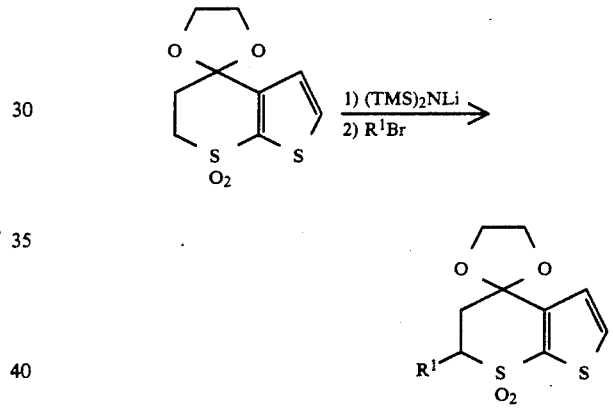

The process comprises treating the 4-oxo compound with ethylene glycol in the presence of an acid catalyst such as toluenesulfonic acid, camphorsulfonic, benzenesulfonic, pyridinium-p-toluenesulfonic acid in an aprotic solvent such as toluene, benzene, or the like at about 80° C. to 120° C., conveniently at reflux temperature under dehydrating conditions such as a Dean-Stark trap, for about 2–10 hours when the reaction is complete.

The resultant ethylenedioxy compound is an important intermediate in the synthesis of compounds with a variety of R$^1$ groups, and forms another embodiment of this invention.

Introduction of the R$^1$ group comprises treating the ethylenedioxy compound in a dry ethereal solvent such as THF, diethyl ether or 1,2-dimethoxyethane, at about −78° C. to −50° C. with a lithiating reagent such as lithium bis(trimethylsilyl)amide (TMS)$_2$NLi for about 0.25 to 1 hour followed by treatment with the R$^1$-Br reagent for about 0.25 to 1 hour and warming to about −10° C. to +10° C. and quenching with water or other protic solvent.

After introduction of the 2-sulfonamide group and regeneration of the 4-oxo group, treatment with an amine of structure RNH$_2$ followed by reduction with a complex metal hydride provides the cis-diastereomer of the desired compound. In practice the 4-oxo compound is dissolved in an ethereal solvent such as THF, diethyl ether or 1,2-dimethoxyethane and treated with an excess of the appropriate amine, R—NH$_2$, in the presence of 3 Å molecular seives or other water scavenger. After 1–4 hours when imine formation is complete, it is treated with a solution of a complex metal hydride such as sodium borohydride in ethanol or methanol at about $-10°$ C. to $+10°$ C. for about 10 minutes to one hour. The reaction can be quenched with aqueous acid.

The trans-diastereomer may be prepared by reduction of a 5,6-dihydro-4H-4-oxo-6-R$^1$-thieno[2,3-b] thiopyran-2-sulfonamide-7,7-dioxide with sodium borohydride to the corresponding cis-4-hydroxy compound; protection of the sulfonamide by formation of the N,N-dimethylformamidine derivative; formation of the cis-4-methanesulfonyl ester; trans-4-azide; trans-4-amino; deprotection of the sulfonamide group; and alkylation of the trans-4-amino compound.

The alkylation is accomplished by adding the appropriate aldehyde, such as acetaldehyde to prepare the compound wherein R is ethyl, to a solution of the trans-4-amino-6-R$^1$-compound in an ethereal solvent such as THF, diethylether or 1,2-dimethoxyethane at about room temperature (15°–25° C.) and stirring for about ½ to 2 hours, usually about one hour. This solution is then added to a solution of a complex metal hydride such as sodium borohydride in a lower alkanol such as ethanol or methanol at about $-10°$ C. to $+10°$ C. and stirred for about ¼ to 1 hour followed by quenching with dilute acid.

The novel pharmaceutical formulations of this invention can be adapted for oral administration such as tablets, capsules or the like; for nasal administration, especially in the form of a spray; for injection, in the form of a sterile injectable liquid; or for topical ocular administration in the form of solutions, ointments, solid water soluble polymeric inserts, or gels.

This invention is particularly concerned with formulations adapted for topical ocular administration for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate; a parasympathomimetic agent such a pilocarpine; an angiotensin converting enzyme inhibitor; a renin inhibitor or a potassium channel agonist. In such combinations the two active agents are present in approximately pharmacologically equivalent amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

(S,S)
(−)5,6-Dihydro-4-ethylamino-6-(n-propyl)-4H-thieno[2,3-b]thiopyran-2-sulfonamide-7,7-dioxide hydrochloride (trans-isomer)

Step A: Preparation of 3-(2-Thienylthio)hexanoic acid (2)

A solution of 2-mercaptothiophene (51.1 g, 0.44 mol), trans-2-hexenoic acid (1) (49.1 g, 0.43 mol), triethylamine (29.3 g, 0.29 mol) in tetrahydrofuran (490 ml) was stirred and refluxed under nitrogen for 21 hours. The mixture was concentrated in vacuo and the residue was distributed between ethyl acetate (500 ml) and 3N hydrochloric acid (200 ml), the aqueous layer was separated and extracted with ethyl acetate (200 ml), the combined ethyl acetate extracts were washed with 3N hydrochloric acid, twice with water and dried over sodium sulfate. The solvent was evaporated in vacuo to yield pale yellow oily product weighing 99 g (100%), which was >96% pure by HPLC.

Step B: Preparation of 5,6-Dihydro-6-(n-propyl)-4H-thieno[2,3-b]thiopyran-4-one (3)

A solution of 2 (99.0 g, 0.43 mol) in dry methylene chloride (415 ml) containing dimethylformamide (2.0 ml) was stirred while oxalyl chloride (59.7 g, 0.47 mol) was added over 30 minutes. The solution was stirred at ambient temperature for 2 hours, then cooled to $-10°$ C. and a solution of stannic chloride (59.9 g, 0.23 mol) in methylene chloride (85 ml) was added over 30 minutes while maintaining the temperature below 0° C. After stirring at 0° C. for 30 minutes, water (210 ml) was added dropwise, keeping the temperature below 10° C. The organic layer was separated, washed with 5% sodium hydroxide solution, twice with water, dried over sodium sulfate and concentrated in vacuo to yield 89.8 g (98%) of light brown, oily product 3. HPLC indicated the material was homogeneous.

Step C: Preparation of 5,6-Dihydro-6-(n-propyl)-4H-thieno[2,3-b]thiopyran-4-one-2-sulfonamide (4)

A solution of 3 (89.8 g, 0.42 mol) in dry methylene chloride (685 ml) was cooled to $-10°$ C. and acetic anhydride (128.6 g, 1.26 mol) was added in one portion with stirring. With continued cooling concentrated sulfuric acid (45.1 g, 0.46 mol) was added dropwise over 15 minutes while maintaining the temperature below $-5°$ C. The mixture was stirred at ambient temperature for 2 hours and the solid then was collected, washed with methylene chloride and dried at 50° C. under vacuum to yield 81.8 g (67%) of the 6-sulfonic acid.

The product was suspended in a mixture of acetonitrile (135 ml) and sulfolane (tetramethylene sulfone, 135 ml) and stirred under nitrogen while triethylamine (28.4 g, 0.28 mol) was added dropwise with occasional cooling to keep the temperature below 30° C. To the pale yellow homogeneous solution was added N,N-dimethylacetamide (9.6 g, 0.11 mol) in one portion and the mixture was stirred at ambient temperature for 30 minutes. Phosphorous oxychloride (49.1 g, 0.32 mol) then was over 20 minutes while maintaining the temperature below 30° C. After stirring at ambient temperature for 22 hours. the mixture was cooled to 10° C. and water (270 ml) was added at such a rate that the temperature did not exceed 25° C. After stirring for 2 hours, the solid was collected, washed with water and dried at 50° C. under vacuum to yield 64.47 g of the intermediary sulfonyl chloride.

The material was dissolved in tetrahydrofuran (575 ml) and added over 30 minutes to a stirred solution of concentrated ammonium hydroxide (290 ml) which previously had been cooled to −15° C. at a rate to maintain the temperature below −5° C. After stirring at ambient temperature for 2 hours, the mixture was concentrated to a volume of approximately 250 ml, water (175 ml) was added and the mixture was stirred for 30 minutes. The pale orange solid was collected and dried at 60° C. under vacuum to yield 56.02 g (46%) of homogeneous product.

An analytical sample melted at 147.5°–148.5° C. after recrystallization from nitromethane.

Anal. Calcd. for $C_{10}H_{13}NO_3S_3$: C, 41.22; H, 4.50; N, 4.81. Found C, 41.24; H, 4.55; N, 4.81.

Step D: Preparation of 5,6-Dihydro-4-hydroxy-6-(n-propyl)-4H-thieno[2,3-b]thiopyran-2-sulfonamide (5)

Sodium borohydride (9.46 g, 0.25 mol) was added over 10 minutes to a stirred suspension of 4 (56.0 g, 0.19 mol) in absolute ethanol (1900 ml) under nitrogen. The mixture was refluxed for 2 hours and stirred at ambient temperature for 20 hours. After acidification with 1N hydrochloric acid (270 ml), followed by addition of saturated sodium bicarbonate solution (200 ml), the mixture was concentrated in vacuo. The residue was distributed between ethyl acetate (1000 ml) and water (600 ml), the aqueous layer was separated and extracted with ethyl acetate (2×600 ml), the combined ethyl acetate extracts were washed with saturated sodium bicarbonate, twice with water and dried over sodium sulfate. Evaporation in vacuo afforded 55.73 g (99%) of homogeneous product.

An analytical sample melted at 156°–157° C. after recrystallization from nitromethane.

Anal. Calcd. for $C_{10}H_{15}NO_3S_3$: C, 40.93; H, 5.15; N, 4.77. Found: C, 40.83; H, 5.29; N, 4.81.

Step E: Preparation of 5,6-Dihydro-4-hydroxy-6-(n-propyl)-4H-thieno[2,3-b]thiopyran-2-sulfonamide-7,7-dioxide (6)

A solution of "oxone" ® (196.7 g, 0.32 mol) in water (870 ml) was added to a stirred solution of 5 (56.6 g, 0.19 mol) in methanol (870 ml) over 45 minutes. After stirring at ambient temperature for 20 hours, the mixture was filtered and the solid washed with methanol. The combined filtrate and washings were concentrated in vacuo below 50° C. to remove methanol. The aqueous suspension was extracted with ethyl acetate (1000 ml and 2×600 ml), the combined extracts were washed twice with water, dried over sodium sulfate and evaporated in vacuo to yield 47.37 g of 6.

The filtered solid from above was stirred with methanol (1000 ml) for 2 hours, filtered and the filtrate was evaporated in vacuo to yield 13.85 g of 6.

The two crops of material were combined and crystallized from nitromethane (400 ml) after treatment with Norit to yield 55.88 g (90%) of product melting at 209.5°–212° C.

Anal. Calcd. for $C_{10}H_{15}NO_5S_3$: C, 36.91; H, 4.65; N, 4.31. Found: C, 36.85; H, 4.48; N, 4.42.

Step F: Preparation of 5,6-Dihydro-4-acetamido-6-(n-propyl)-4H-thieno[2,3-b]thiopyran-2-sulfonamide-7,7-dioxide (7)

A suspenison of 6 (47.41 g, 0.146 mol) in acetonitrile (500 ml) was chilled to −10° C. The cold stirring suspension was treated with 95% $H_2SO_4$ (165.5 ml, 3.11 mol) at a rate sufficient to maintain the temperature below 0° C. After equilibrating to room temperature overnight, the resulting solution was poured over ice and was stirred for 4.0 hours. The resulting aqueous suspension was partitioned between 1000 ml and 250 ml of ethyl acetate. The aqueous phase was collected, buffered to pH 8, and partitioned with an additional 50 ml of ethyl acetate. All organic phases were combined and washed with 250 ml of saturated aqueous sodium bicarbonate followed by washing with 250 ml of saturated aqueous sodium chloride. The dried ($Na_2SO_4$) organic phase was filtered and concentrated to give 55.27 g (quantitative) of 7 as an orange foam.

Step G: Preparation of Trans-5,6-dihydro-4-ethylamino-6-(n-propyl)-4H-thieno[2,3-b]thiopyran-2-sulfonamide-7,7-dioxide (8)

A flask fitted with a short path distillation head was charged with a solution of 7 (53.3 g, 0.145 mol) in 1000 ml of tetrahydrofuran. After blanketing the system with argon, the solution was treated with 10.0M $BH_3.(CH_3)_2S$ (51 ml, 0.5 mol) at a rate sufficient to maintain reasonable gas evolution. Upon addition, the flask was gently warmed to collect $(CH_3)_2S$. After equilibrating to room temperature overnight, the solution was chilled to 0° C. and was then treated with 80 ml of absolute ethanol followed by equilibrating to room temperature. The resulting amber solution was concentrated to remove solvents. The dry solids were solublilzed in 500 ml of tetrahydrofuran and treated with 60 ml (0.36 mol) of 6N aqueous hydrochloric acid. The mixture was allowed to reflux for 1 hour, followed by stirring at room temperature for 2 hours. The solution was concentrated to remove tetrahydrofuran, and the resulting oil was treated with 500 ml of ethyl acetate and 200 ml of water. The aqueous phase was buffered to pH 8, and washed with an additional 50 ml of ethyl acetate. All organic extracts were then washed with 100 ml of saturated aqueous sodium chloride. The dried ($Na_2SO_4$) organic phase was filtered and concentrated to yield 45.12 g (0.128 mol, 88.3%) of 8 and 9 as a cis/trans isomeric mixture. The mixture was dissolved in 1500 ml ethyl acetate and treated with a solution of 5.6 g (0.134 mol) of maleic acid in 400 ml of hot ethyl acetate. A sufficient amount of hot methanol was added to solubilize all solids, and the solution was allowed to stand for 72 hours. The resulting white solid was collected and dried to give 12.50 g of the maleate salt. A second crop gave 2.26 g. The remaining liquor was concentrated and oil was solubilized in ethyl acetate and triturated slowly with diethyl ether to selectively give the trans isomer. The precipitation was repeated several times to give a total of 12.88 g of white solid. The total amount of pure trans maleate was 27.64 g (46.1% of 8). The remaining cis isomer enriched oil 9 was chromatographed (silica gel, 95:5:0.5, $CHCl_3/MeOH/NH_4OH$ followed by 90:10:1.0, $CHCl_3/MeOH/NH_4OH$)) to give 0.9 g of 8. A total yield of 21.70 g (48.4% yield)* of 8 was obtained.

Step H: Preparation of (S,S)(−) 5,6-Dihydro-4-ethylamino-6-(n-propyl)-4H-thieno[2,3-b]thiopyran-2-sulfonamide-7,7-dioxide hydrochloride trans- isomer (10)

A boiling solution of 8 (14.4 g, 0.041 mol) in absolute ethanol (260 ml) was treated with di-p-toluoyl-L-tartaric acid monohydrate (4.04 g, 0.010 mol). After standing overnight at ambient temperature, the salt was collected, dried and recrystallized twice more from absolute ethanol (125–170 ml) after treatment with decolorizing carbon to yield 4.60 g of salt melting at 153°–154° C. (dec).

The free base was prepared by distributing the salt between ethyl acetate (150 ml) and saturated sodium bicarbonate solution (75 ml). The aqueous layer was separated and extracted with ethyl acetate (2×100 ml), the combined extracts were washed twice with water, dried over sodium sulfate and evaporated in vacuo to yield 2.89 g of white solid.

The hydrochloride salt was prepared by dissolving the free base (2.89 g, 0.0082 mol) in boiling absolute ethanol (100 ml), adding 2.0 ml of 7.1N ethanolic HCl and allowing the white solid to crystallize at ambient temperature. The product weighed 3.04 g and melted at 274.5°–275° C.; $[\alpha]_D^{25} -15.37°$ C. ($CH_3OH$).

Anal. Calcd. for $C_{12}H_{20}N_2O_4S_3 \cdot HCl$: C, 37.05; H, 5.44; N, 7.20. Found: C, 37.31; H, 5.54; N, 7.24.

Following the procedures substantially as described in Example 1 but substituting for the starting materials used therein, the appropriate carboxylic acid Step A of structure:

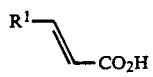

and the appropriate nitrile of structure $CH_3CN$ or $C_2H_5CN$ there are prepared the compounds described in the following Table I:

TABLE I

| R | $R^1$ | isomer | m.p. (°C.) |
|---|---|---|---|
| n-$C_3H_7$— | n-$C_3H_7$— | trans(±) | 173–174(HCl) |
| n-$C_3H_7$— | n-$C_3H_7$— | trans(−) | 231–233(HCl) |
| $C_2H_5$— | i-$C_3H_7$— | — | — |
| n-$C_3H_7$— | i-$C_3H_7$— | — | — |

EXAMPLE 2 cis-6-Allyl-5,6-dihydro-4H-4-ethylaminothieno[2,3-b]thiopyran-2-sulfonamide-7,7-dioxide hydrochloride Step A: Preparation of 3-(2-thienylthio)propanoic acid In a 2-L, three-necked round-bottomed flask fitted with a thermometer, nitrogen inlet, mechanical stirrer and addition funnel was placed thiophene (64 mL, 799 mmol;) and sieve dried THF (400 mL, residual water≦120 μg/mL). The solution was cooled to 0°–5° C. and 1.6M n-butyllithium (470 mL, 751 mmol) was added at such a rate as to maintain the temperature at <20° C. The reaction was stirred for 1 hour at 0°–5° C., and was used immediately in the next sequence.

To the cooled reaction mixture (0°–5° C.) was added sulfur (24 g, 750 mmol) portionwise while maintaining the temperature at <20° C. The reaction was stirred for an additional 2.0 hour at 0°–5° C. after which nitrogen-purged water (300 mL) was added at such a rate as to maintain the temperature at <18° C. The addition of sulfur was highly exothermic. (Note: The 2-mercaptothiophene and its anion can air-oxidize to the corresponding disulfide. Therefore, solutions of 2-mercaptothiophene must be deoxygenated and stored under a nitrogen atmosphere). Solids may form initially upon addition of water to the solution of 2-mercaptothiophene but eventually dissolve.

In a 1-L, 3-necked, round-bottomed flask fitted with an addition funnel, thermometer, nitrogen sweep and mechanical overhead stirrer was prepared a solution of potassium carbonate (46.5 g, 337 mmol) in nitrogen-purged water (85 mL). To this solution was added solid 3-bromopropionic acid (116 g, 736 mmol) at such a rate as to control foaming ($CO_2$ evolution). The mixture was stirred until a clear solution was obtained. The temperature increased from 23° C. to 50° C. during the dissolution of potassium carbonate. (Note: Foaming occurs during the addition of 3-bromopropionic acid to the potassium carbonate solution with the evolution of carbon dioxide). The solution was cooled to 10° C. and the aqueous solution of potassium 3-bromopropionate was added at such a rate as to maintain the temperature at 0°–5° C. The reaction was stirred for 24 hours at ambient temperature. The layers were separated and the aqueous layer was washed twice with toluene (100 mL portions) to remove neutral organic impurities. The aqueous layer was then cooled to 10° C. and stirred with toluene (300 mL) as aqueous HCl (125 mL, 6N) was added, maintaining the temperature at <14° C. (pH<1). The organic layer was separated and the aqueous layer extracted with additional toluene (300 mL). The organic layers were combined and dried azeotropically under vacuum to a volume of 500 mL and residual water of ≦2.5 mg/mL. The solution was stored at 0°–5° C. overnight. A small amount of the carboxylic acid was isolated and characterized as its tert-butylammomium salt: m.p. 110°–112° C.

Anal. Calcd for $C_{11}H_{19}NO_2S_2$: C, 50.54; H, 7.33; N, 5.36. Found: C, 50.53; H, 7.12; N, 5.27.

Step B: Preparation of 5,6-dihydro-4H-thieno[2,3-b]thiopyran-4-one

In a 2-L reactor fitted with an overhead mechanical stirrer, thermometer, addition funnel, reflux condenser, and nitrogen bubbler vented through an acid-vapor scrubber was placed the toluene solution of product from Step A (130.7 g, 695 mmol). The reaction mixture was brought to an initial temperature of 20° C. and trifluoroacetic anhydride (161 g, 765 mmol) was added over 5 minutes to the stirred solution. The reaction was then heated to 35°–38° C. and stirred for about 1.5 hours. The reaction mixture was then slowly added to water (500 mL) maintaining the temperature at <25° C. A pH probe was placed in the vessel and the mixture was titrated to pH 7.0 with 50% sodium hydroxide (123 g, 1.53 mole). The layers were separated and the aqueous phase was extracted once with toluene (200 mL). The combined organic extracts were then concentrated under vacuum (43 mBar) to a volume of 200 mL and then diluted to 1.2 L with ethyl acetate for the next step (oxidation). A small sample was chromatographed to obtain the following data: $R_f = 0.29$ (85:15 hexane:ethyl acetate). m.p. 61°–62° C. $^1H$ NMR: δ 7.42 (d, J=5.4, $H_2$); 6.98 (d, J=5.4 $H_3$); 3.33 (m, $C_5H_2$); 2.82 (m, $C_6H_2$). $^{13}C$ NMR: $δ_c$ 188.9 ($C_4$), 150.9, 135.0 ($C_{3a}$, $C_{7a}$), 126.1, 121.8 ($C_2$, $C_3$), 38.1 ($C_6$), 30.0 ($C_5$). Anal Calcd for $C_7H_6OS_2$: C, 49.39; H, 3.55; S, 37.66. Found: C, 49.56; H, 3.58; S, 37.68.

Step C: Preparation of 5,6-dihydro-4H-thieno[2,3-b]thiopyran-4-one-7,7-dioxide

The ethyl acetate/toluene solution of ketone from Step B (118 g, 765 mmol in 1.2 L of 5:1 v:v ethyl acetate/toluene) was charged to a 5-L three-necked round-bottomed flask equipped with an overhead mechanical stirrer, 250-mL pressure-equalizing dropping funnel, and thermocouple temperature probe. The mixture was stirred and water (35 mL) was added to saturate the organic phase. A solution of sodium tungstate dihydrate (11.7 g, 77 mmol) dissolved in water (35 mL) was then added (caution: there is an induction period of several minutes before an exotherm). The mixture was heated to 35° C. and hydrogen peroxide (30%, 250 mL, 2.43 mole) was added over 45 minutes. The temperature of the reaction was allowed to rise to 55°-58° C. until judged complete by HPLC: 4.1×254 mm Altex C-8, 5-micron ultrasphere column at 45° C. (2 mL/min, gradient from 65:35 to 20:80 0.1% $H_3PO_4$ in $H_2O$: $CH_3CN$ over 20 minutes, then isocratic for 5 minutes 230 nm) $R_1$ (sulfoxide) 6.9 minutes, (sulfone) 10.6 minutes, (sulfide) 15.8 minutes. On completion the mixture was cooled to 0°-5° C. and excess hydrogen peroxide was decomposed by the slow addition of aqueous sodium sulfite (205 g, 1.63 mole dissolved in 700 mL water). The temperature of the reaction mixture was maintained at <20° C. When the reaction mixture tested negative for peroxides with acidified starch-iodide paper, the layers were separated. The upper organic layer was concentrated under vacuum at 45° C. bath temperature to a volume of 400 mL. Hexanes (400 mL) were then added over approximately 10 minutes and the batch was aged for one hour. The product was filtered, washed with hexanes, and dried under vacuum at 60° C. with a nitrogen sweep to constant weight. The yield of crude ketosulfone was 113 g (76% from 3-bromopropionic acid). Crude ketosulfone was then recrystallized from methanol in the following procedure. A quantity of 113 g crude ketosulfone was dissolved in 3 L of anhydrous methanol at 55°-60° C. The solution was cooled to 40° C. and 10 g of Calgon ADP ® carbon was added. The mixture was aged at 40° C. for a minimum of 4 hours. The batch was then filtered warm at 40° C. through a well-washed pad of SuperCel ®. The filter cake was washed with two 500 mL portions of methanol at 40° C. and filtrates were combined. The batch was then concentrated under vacuum to a volume of 500 mL and aged at 0°-5° C. for 4 hours. Crystallization ensured during concentration. The batch was filtered, washed with 75 mL cold methanol, sucked dry under nitrogen, and dried under vacuum (25" Hg) at 80° C. with a nitrogen sweep for 12 hours. The recovery yield was 100 g (89%) assayed @ 99.6 wt % by HPLC against an external standard. $R_f$=0.30 (dichloromethane). m.p. 121°-121.5° C. $^1H$ NMR: δ 7.60 (d, J=5.1, $H_2$); 7.50 (d, J=5.1, $H_3$); 3.76 (m, $C_5H_2$); 3.36 (m, $C_6H_2$).

$^{13}C$ NMR: $δ_c$ 186.3 ($C_4$), 147.2 ($C_{3a}$), 139.3 ($C_{7a}$), 130.2 ($C_2$), 126.3 ($C_3$), 52.8 ($C_6$), 37.0 ($C_5$). MS (EI, 70 eV): 202 (M+, 35), 174 (38), 138 (15), 110 (100), 84 (30), 82 (25).

Anal Calcd for $C_7H_6O_3S_2$: C, 41.57; H, 2.99; S, 31.70. Found: C, 41.49; H, 3.02; S, 31.60.

Step D: Preparation of 5,6-Dihydro-4H-4-(spiro-2',5'-dioxolanyl)thieno[2,3-b]thiopyran-7,7-dioxide To a 5 L 4-necked round bottom flask fitted with a condenser, Dean-Stark trap, $N_2$ inlet, and mechanical stirrer a mixture of 5,6-dihydro-4H-4-oxothieno[2,3-b]thiopyran-7,7-dioxide (100 g, 0.495 mol), toluenesulfonic acid (2.8 g), ethylene glycol (276 mL, 4.95 mol) in toluene (2.8 L) was brought to reflux. Water collected in the trap over a period of 5 h, at which time tlc showed that the reaction was complete. The reaction was cooled to room temperature and toluene was removed in vacuo. The residue was partitioned between chloroform (3 L) and 5% NaOH (200 mL). The organic phase was washed with saturated brine and dried over magnesium sulfate. The solution was filtered and the solvent removed in vacuo to give 112 g of crude product. This material was recrystallized from n-butylchloride (2.3 L) and dried in vacuo to give light tan crystals (89 g). A second crop yielded additional product (9.5 g). Combined yield is 98.5 g, 81% yield.

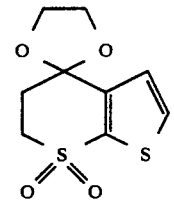

Step E: Preparation of 6-Allyl-5,6-dihydro-4H-4-(spiro-2',5'-dixolanyl)thieno[2,3-b]thiopyran-7,7-dioxide A magnetically stirred solution of 5,6-dihydro-4H-4-(spiro-2',5'-dioxolanyl)thieno[2,3-b]thiopyran-7,7-dioxide (10.00 g, 0.0406 mol) in dry THF (250 mL) was cooled to −78° C. under a nitrogen atmosphere. Lithium bis(trimethylsilyl)amide (42.6 mL, 1M in THF) was added via syringe. After stirring for 0.5 h allyl bromide (4.5 mL, 0.052 mol) was added. After an additional 0.5 h the reaction was warmed to 0° C. and approximately 10 mL water was added. The THF was removed in vacuo and the residue partitioned between ethyl acetate and water. The ethyl acetate was washed with saturated brine and dried over magnesium sulfate. The solution was filtered and the solvent removed in vacuo to give a red oil which solidified on standing. This material was chromatographed using medium pressure chromatography on silical gel with 20% ethyl acetate in hexane serving as eluant. The title compound was obtained as a white waxy solid, mp=75°-76° C. (9.93 g, 85% yield). Anal. Calc. for $C_{12}H_{14}O_4S_2$: C, 50.33; H, 4.92. Found: C, 50.09; H, 4.72.

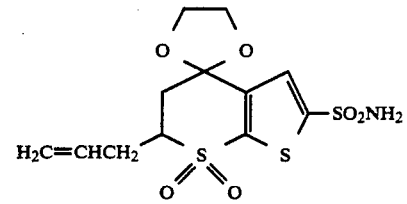

Step F: Preparation of 6-Allyl-5,6-dihydro-4H-4-(spiro-2',5'-dioxolanyl)thieno[2,3-b]thiopyran-2-sulfonamide-7,7-dioxide A solution of LDA was generated by the addition of n-butyllithium (25.8 mL, 2.5M in hexane) to diisopropylamine (9.28 mL) in dry THF (200 mL) at −78° C. under $N_2$. The clear solution was stirred for 40 min. In a separate flask, 6-allyl-5,6-dihydro-4H-4-(spiro-2',5'-dioxolanyl)thieno[2,3-b]thiopyran-7,7-dioxide (18.06 g, 0.0631 mol) was dissolved in dry THF (200 mL) and cooled to −78° C. under $N_2$. The LDA solution was transferred by cannula to this flask over a period of 5-10 min. The previously clear solution becomes orange-red as deprotonation proceeds. This reaction was stirred for 0.5 h at −78° C., then added by cannula to an excess of sulfur dioxide in THF at −78° C. over a period of 20 min. The red color discharged immediately upon quenching. The reaction was allowed to warm to 0° C. and the THF removed in vacuo. The resulting foam was dissolved in 10% sodium acetate in water (200 mL) to give a solution with pH=7. The aqueous solution was extracted with ethyl acetate (1×200 mL) to remove unreacted starting material. The aqueous phase was adjusted to pH 6 by the addition of glacial acetic acid (2 mL). Hydroxylamine-O-sulfonic acid (10.7 g, 0.094 mol) was added to the solution of sulfinate salt and the reaction stirred at room temperature overnight. The white precipitate which formed was filtered from the reaction mixture, washed with water and dried in vacuo at 60° C. to give the crude product as a white granular solid (16.1 g). This material was recrystallized from 1,2-dichloroethane to give the title compound as a light tan powder, mp=188.0°-190.5° C. (12.5 g, 54%).

Anal. Calc. for $C_{12}H_{15}NO_6S_3$: C, 38.44; H, 4.13; N, 3.83. Found: C, 38.83; H, 3.97; N, 3.81.

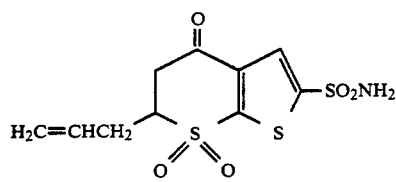

Step G: Preparation of 6-Allyl-5,6-dihydro-4H-4-oxothieno[2,3-b]thiopyran-2-sulfonamide-7,7-dioxide 6-Allyl-5,6-dihydro-4H-4-(spiro-2',5'-dioxolanyl)-thieno[2,3-b]thiopyran-2-sulfonamide-7,7-dioxide (5.70 g, 0.015 mol) was dissolved in 1:1 THF and 5N HCl (200 mL). The clear solution was heated to reflux whereupon tlc showed the reaction was complete ($R_f$ ketal—0.39, $R_f$ ketone—0.52 in 1:1 ethyl acetate/hexane). The reaction was cooled to room temperature, THF was removed in vacuo and the aqueous acid extracted with ethyl acetate. The organic extract was washed with saturated brine and dried over magnesium sulfate. The solvent was removed in vacuo and the resulting oil triturated with n-butylchloride to give the title compound as a white solid (4.6 g, 91% yield).

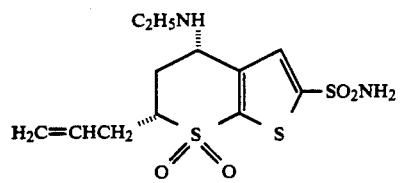

Step H: Preparation of cis-6-Allyl-5,6-dihydro-4H-4-ethylaminothieno[2,3-b]thiopyran-2-sulfonamide-7,7-dioxide hydrochloride 6-Allyl-5,6-dihydro-4H-4-oxothieno[2,3-b]thiopyran-2-sulfonamide-7,7-dioxide (2.0 g, 6.1 mmol) was dissolved in dry THF (80 mL) and 3 Å molecular sieves added to the reaction mixture. An excess of ethylamine was added and the reaction stirred for 2 h under $N_2$. Sodium borohydride (1.2 g, 30 mmol) in absolute ethanol was added to the stirred solution of imine at 0° C. After 15 minutes the reaction was quenched with 10% aqueous HCl until pH=1. Ethanol was removed in vacuo and the aqueous solution extracted with ethyl acetate; The phases were separated and the aqueous phase adjusted to pH 8 with sodium hydroxide. The aqueous phase was extracted with ethyl acetate and the ethyl acetate extract washed with saturated brine and dried over magnesium sulfate. Filtration and evaporation solvent gave the crude product which was chromatographed on silica gel with 5% chloroform in methanol to give the title compound as a white solid (1.5 g, 70% yield). This compound was resolved with (+) di-p-toluoyl-D-tartaric acid and converted to the HCl salt as described previously to give the (+) isomer of the title compound, mp=242°-245° C.: $[\alpha]_D = +83.8$ Anal: Calc. for $C_{12}H_{18}N_2O_4S_3 \cdot HCl \cdot H_2O$: C, 35.59; H, 5.22; N, 6.91. Found: C, 35.46; H, 5.07; N, 6.81.

Employing the precedures substantially as described in Example 2, Steps A through H, but substituting for the allyl bromide used in Step E thereof and the ethylamine used in Step H thereof equivalent amounts of a $C_{3-5}$ hydrocarbyl bromide of structure $R^1$—Br and an amine of structure $RNH_2$ as shown in Table II respectively there are produced the compounds also described in Table II.

TABLE II

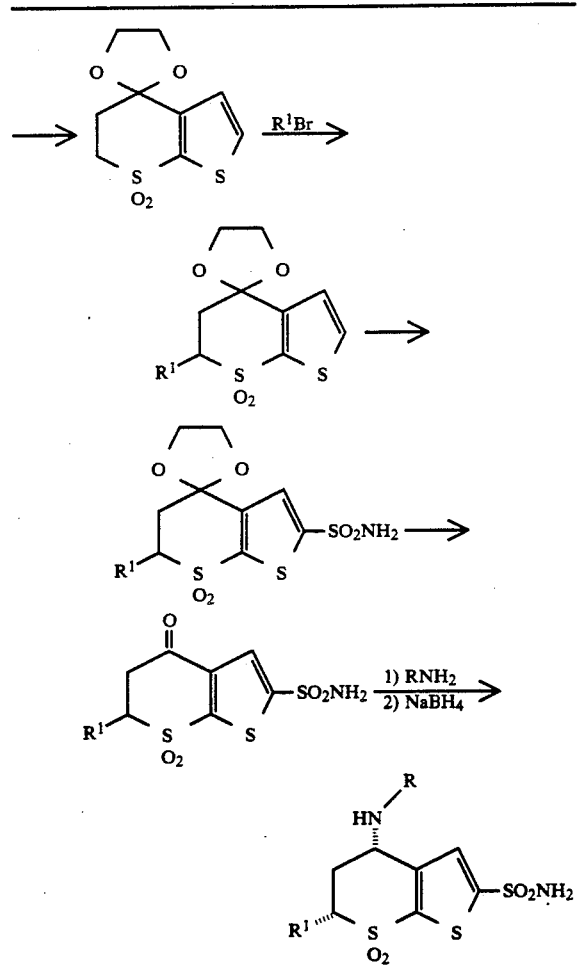

| $R^1$ | R |
|---|---|
| n-$C_3H_7$— | $C_2H_5$— |
| n-$C_3H_7$— | n-$C_3H_7$— |
| n-$C_3H_7$— | i-$C_3H_7$— |
| i-$C_3H_7$— | $C_2H_5$— |
| n-$C_4H_9$— | $C_2H_5$— |
| $H_2C$=$CHCH_2$— | n-$C_3H_7$— |
| n-$C_5H_{11}$— | $C_2H_5$— |
| $H_3C$—$CH$=$CH$—$CH_2$— | $C_2H_5$— |

TABLE II-continued

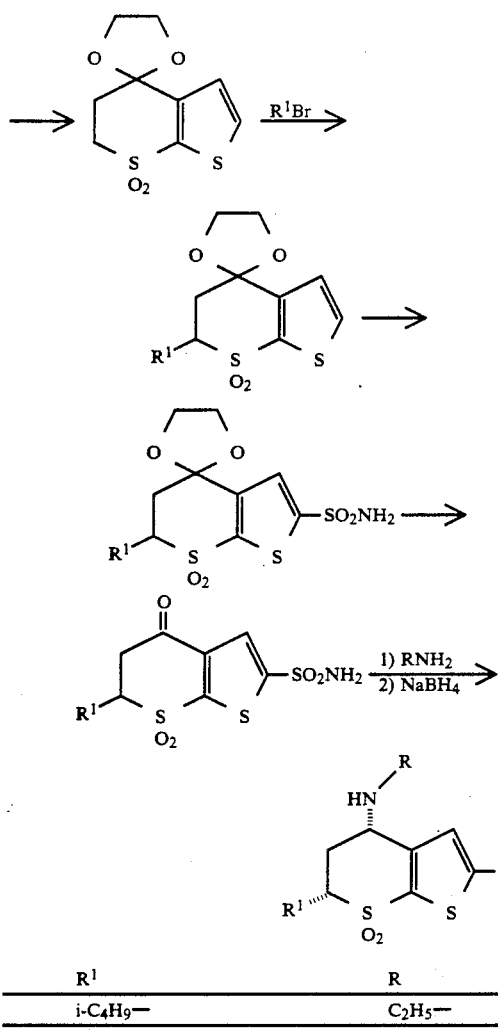

| R¹ | R |
|---|---|
| i-C₄H₉— | C₂H₅— |

EXAMPLE 3

Trans-6-Allyl-5,6-dihydro-4-ethylamino-4H-thieno[2,3-b]thiopyran-2-sulfonamide-7,7-dioxide

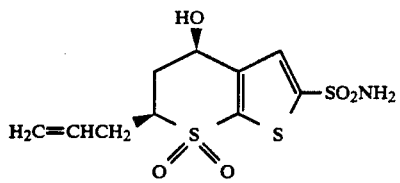

Step A: Preparation of cis-6-Allyl-5,6-dihydro-4H-4-hydroxythieno[2,3-b]thiopyran-2-sulfonamide-7,7-dioxide A solution of 6-allyl-5,6-dihydro-4H-4-oxothieno[2,3-b]thiopyran-2-sulfonamide-7,7-dioxide (4.6 g, 0.014 mol) in methanol was cooled with stirring to 0° C. and sodium borohydride (0.54 g, 0.014 mol) added portionwise. After 15 minutes the reaction was quenched by the addition of water. The quenched reaction was stirred at 0° C. for 0.5 h and the methanol removed in vacuo. The aqueous solution was rendered acidic with 10% aqueous HCl and extracted with ethyl acetate; the phases were separated and the aqueous phase adjusted to pH 8 with sodium hydroxide. The weakly basic aqueous phase was extracted with ethyl acetate, and the ethyl acetate washed with saturated brine and dried over magnesium sulfate. The solution was filtered and the solvent in vacuo to give the title compound as a white powder (4.24 g, 93% yield).

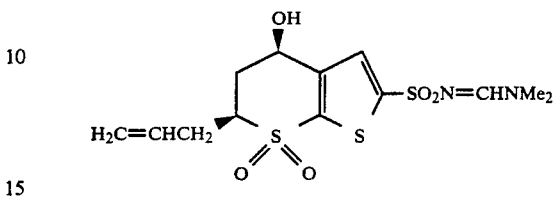

Step B: Preparation of N'-(cis-6-Allyl-5,6-dihydro-4H-4-hydroxythieno[2,3-b]thiopyran-2-sulfonyl)N,N-dimethylformamidine-7,7-dioxide cis-6-Allyl-5,6-dihydro-4H-4-hydroxythieno[2,3-b]thiopyran-2-sulfonamide-7,7-dioxide (4.24 g, 13.11 mmol) was dissolved in acetonitrile (100 mL) and N,N-dimethylformamide dimethyl acetal (2.44 mL, 18.3 mmol) was added with stirring. After 15 minutes the solvents were removed in vacuo and the residue partitioned between 1N HCl and ethyl acetate. The phases were separated and the organic phase washed with saturated brine. The ethyl acetate solution was dried over magnesium sulfate, filtered and evaporated to give the title compound as a tan solid (5.06 g, 100%).

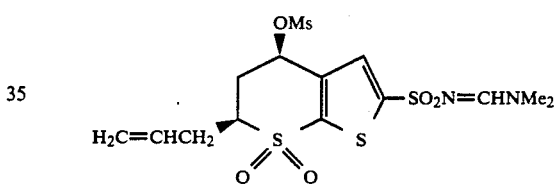

Step C: Preparation of N'-(cis-6-Allyl-5,6-dihydro-4H-4-methanesulfonyloxythieno[2,3-b]thiopyran-2-sulfonyl)N,N-dimethylformamidine-7,7-dioxide N'-(cis-6-Allyl-5,6-dihydro-4H-4-hydroxythieno[2,3-b]thiopyran-2-sulfonyl)N,N-dimethylformamidine-7,7-dioxide (5.06 g, 13.3 mmol) was dissolved in dry THF (100 mL) and triethylamine (5.61 mL, 40.1 mmol) was added. The stirred solution was cooled under N₂ and methanesulfonic acid anhydride (2.79 g, 16.0 mmol) was added. The suspension was stirred at room temperature; after 5 minutes complete dissolution had occured. After 1 hour, the solvent was removed in vacuo and the reside partitioned between ethyl acetate and water. The ethyl acetate was washed with saturated brine, dried over magnesium sulfate, filtered and evaporated to give the title compound as a white solid (6.06 g, 99% yield).

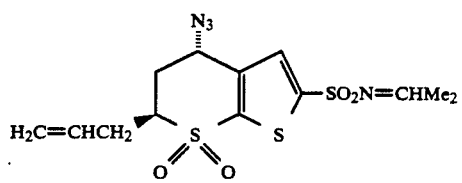

Step D: N'-(trans-6-Allyl-4-azido-5,6-dihydro-4H-thieno[2,3-b]thiopyran-2-sulfonyl)N,N-dimethylformamidine-7,7-dioxide Sodium azide (1.02 g, 15.8 mmol) was added to a solution of N'-(cis-6-allyl-5,6-dihydro-4H-4-methanesulfonyloxythieno[2,3-b]thiopyran-2-(sulfonyl) N,N-dimethylformamidine-7,7-dioxide (6.0 g, 13.1 mmol) in DMSO (150 mL). The reaction was stirred at room temperature overnight. The reaction was diluted with water (200 mL) and extracted with ethyl acetate (400 mL). The ethyl acetate solution was extracted with additional water (4×150 mL), saturated brine, dried over magnesium sulfate, filtered and evaporated to give the title compound as a foam (5.21 g, 98% yield).

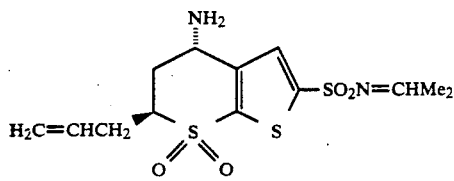

Step E: N'-(trans-6-Allyl-4-amino-5,6-dihydro-4H-thieno[2,3-b]thiopyran-2-sulfonyl)N,N-dimethylformamidine-7,7-dioxide Triphenylphosphine (3.41 g, 13.0 mmol) was added to a solution of N'-(trans-6-allyl-4-azido-5,6-dihydro-4H-thieno[2,3-b]thiopyran-2-sulfonyl)N,N-dimethylformamidine-7,7-dioxide (5.21 g, 12.9 mmol) in THF (100 mL). The reaction was stirred for 3 hours, then water (20 mL) added and the reaction refluxed for 4 hours. The reaction was cooled to room temperature and the THF evaporated in vacuo. The aqueous portion was extracted with ethyl acetate. The ethyl acetate was washed with saturated brine, dried over magnesium sulfate, filtered and evaporated to give the title compound as a foam (3.5 g, 72% yield).

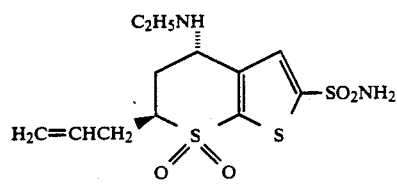

Step F: Preparation of trans-6-Allyl-5,6-dihydro-4-ethylamino-4H-thieno[2,3-b]thiopyran-2-sulfonamide-7,7-dioxide hydrochloride Acetaldehyde (0.5 mL) was added to a solution of N'-(trans-6-allyl-4-amino-5,6-dihydro-4H-thieno[2,3-b]thiopyran-2-sulfonyl)N,N-dimethylformamidine-7,7-dioxide (3.5 g, 9.3 mmol) in THF (50 mL) and the reaction stirred at room temperature under $N_2$ for 45 minutes. This solution was added to sodium borohydride (1.8 g, 45 mmol) in ethanol (50 mL) at 0° C. After 15 minutes the reaction was quenched by the slow addition of 10% aqueous HCl. When gas evolution ceased methanol was removed in vacuo and the remaining acidic aqueous solution extracted with ethyl acetate. The aqueous phase was adjusted to pH=8 and extracted with ethyl acetate. The ethyl acetate solution was washed with brine, dried over magnesium sulfate, filtered and evaporated to give the crude product. This was chromatographed on silica gel with 5% chloroform in methanol to give the title compound as a white solid (2.0 g, 61% yield). This compound was resolved with (−) di-p-toluoyl-L-tartaric acid and converted to the HCl salt as described previously to give the (−) isomer of the title compound, mp=269°-271° C.: $[\alpha]_D = -30.3$.

Anal: Calc. for $C_{12}H_{18}N_2O_4S_3$·HCl: C, 37.24; H, 4.95; N, 7.24. Found: C, 37.35; H, 5.04; N, 7.18.

Employing the procedures substantially as described in Example 3, Steps A through F, substituting for the acetaldehyde used in Step F thereof equivalent amounts of acetaldehyde, propionaldehyde or acetone respectively as shown in Table III there are produced the compounds also described in Table III.

TABLE III

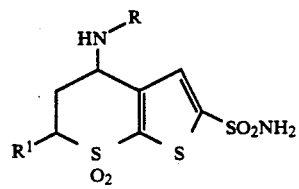

| $R^1$ | R |
|---|---|
| n-C₃H₇— | C₂H₅— |
| n-C₃H₇— | n-C₃H₇— |
| n-C₃H₇— | i-C₃H₇— |
| i-C₃H₇— | C₂H₅— |
| n-C₄H₉— | C₂H₅— |
| H₂C=CHCH₂— | n-C₃H₇— |
| n-C₅H₁₁— | C₂H₅— |
| H₃C—CH=CH—CH₂— | C₂H₅ |
| i-C₄H₉— | C₂H₅ |

EXAMPLE 4

| Eye Drops | | |
|---|---|---|
| (S,S)(−)5,6-dihydro-4H-4-ethylamino-6-(n-propyl)-thieno[2,3-b]thiopyran-2-sulfonamide-7,7-dioxide.HCl | 1 mg | 15 mg |
| monobasic sodium phosphate.2H₂O | 9.38 mg | 6.10 mg |
| dibasic sodium phosphate.12H₂O | 28.48 mg | 16.80 mg |
| benzalkonium chloride | 0.10 mg | 0.10 mg |
| water (for injection) q.s. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

What is claimed is:

1. A compound of structural formula:

or diastereomers or enantiomers or mixtures thereof or an ophthalmologically acceptable salt thereof wherein:
R is ethyl, n-propyl or isopropyl; and
$R^1$ is
a) C₃₋₅ alkyl, b) C$_{3-5}$ alkenyl, or c) C$_{3-5}$ alkynyl.

2. The compound of claim 1 wherein R is ethyl and R$^1$ is n-propyl.

3. The compound of claim 1 wherein R is ethyl and R$^1$ is allyl.

4. The compound of claim 2 which is the trans (S,R) diastereomer or cis (S,R) diastereomer.

5. The compound of claim 3 which is the trans (S,R) diastereomer or cis (S,R) diastereomer.

6. The compound of claim 4 which is the trans (S,S)(−)-enantiomer or cis (S,R)(+)-enantiomer.

7. The compound of claim 5 which is the trans (S,S)(−)-enantiomer or cis (S,R)(+)-enantiomer.

8. A compound of structural formula

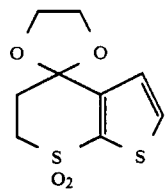

9. An ophthalmological formulation for the treatment of ocular hypertension and glaucoma comprising an opthalmologically acceptable carrier and the compound of claim 1.

10. A method of treating ocular hypertension and glaucoma which comprises the topical ocular administration of an effective amount of the compound of claim 1 to a patient in need of such treatment.

* * * * *